(12) United States Patent
Lueken et al.

(10) Patent No.: US 7,179,947 B2
(45) Date of Patent: Feb. 20, 2007

(54) PROCESS FOR THE HYDROFORMYLATION OF OLEFINS

(75) Inventors: Hans-Gerd Lueken, Marl (DE); Alfred Kaizik, Marl (DE); Stefan Drees, Duelmen (DE); Wilfried Bueschken, Haltern am See (DE); Wilhelm Droste, Marl (DE)

(73) Assignee: Oxeno Olefinchemie GmbH, Marl (DE)

(*) Notice: Subject to any disclaimer, the term of this patent is extended or adjusted under 35 U.S.C. 154(b) by 0 days.

(21) Appl. No.: 11/291,858

(22) Filed: Dec. 2, 2005

(65) Prior Publication Data

US 2006/0128998 A1 Jun. 15, 2006

(30) Foreign Application Priority Data

Dec. 9, 2004 (DE) .................... 10 2004 059 293

(51) Int. Cl.
*C07C 45/50* (2006.01)

(52) U.S. Cl. ...................... 568/451; 568/453

(58) Field of Classification Search ................ None
See application file for complete search history.

(56) References Cited

U.S. PATENT DOCUMENTS

| | | | |
|---|---|---|---|
| 4,658,068 A * | 4/1987 | Hanin | 568/451 |
| 5,177,282 A | 1/1993 | Nierlich et al. | |
| 6,015,928 A | 1/2000 | Gubisch et al. | |
| 6,184,424 B1 | 2/2001 | Bueschken et al. | |
| 6,239,318 B1 | 5/2001 | Schuler et al. | |
| 6,331,657 B1 | 12/2001 | Kaizik et al. | |
| 6,403,836 B2 | 6/2002 | Kaizik et al. | |
| 6,407,295 B1 | 6/2002 | Kaizik et al. | |
| 6,482,992 B2 | 11/2002 | Scholz et al. | |
| 6,720,457 B2 | 4/2004 | Drees et al. | |
| 6,723,884 B1 | 4/2004 | Grenacher et al. | |
| 6,960,699 B2 | 11/2005 | Toetsch et al. | |
| 2005/0209489 A1 | 9/2005 | Moller et al. | |

FOREIGN PATENT DOCUMENTS

| | | |
|---|---|---|
| DE | 196 54 340 A1 | 8/1998 |
| DE | 198 42 368 A1 | 3/2000 |
| DE | 198 42 369 A1 | 3/2000 |
| DE | 198 42 370 A1 | 3/2000 |
| DE | 198 42 371 A1 | 3/2000 |
| DE | 199 39 491 A1 | 2/2001 |
| DE | 100 09 207 A1 | 8/2001 |
| DE | 100 34 360 A1 | 1/2002 |
| DE | 101 35 906 A1 | 2/2003 |
| DE | 102 27 995 A1 | 9/2003 |
| DE | 102 41 266 A1 | 3/2004 |
| EP | 0 213 639 A2 | 3/1987 |
| EP | 0 214 622 A2 | 3/1987 |
| EP | 1 057 803 A1 | 12/2000 |
| WO | WO 92/13818 | 8/1992 |
| WO | WO 2004/020380 A1 | 3/2004 |
| WO | WO 2004/024661 A1 | 3/2004 |

OTHER PUBLICATIONS

J. Falbe, "New syntheses with carbon monoxide", Springer Verlag, 1980, pp. 95-100 and 158-179 and a cover page.
R. H. Friedlander, et al., "Make plasticizer olefins via n-butene dimerization", Hydrocarbon Processing, Feb. 1986, p. 31-33.

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

A process for the catalytic hydroformylation of olefins having from 6 to 24 carbon atoms, in which the hydroformylation is carried out in one or more stage(s) and a mixture comprising at least one olefin and an aldehyde in a molar ratio of aldehyde to olefin of from 0.005:1 to 0.2:1 is used as feed in at least one of these stages which is carried out in the presence of an unmodified cobalt complex as catalyst.

16 Claims, 3 Drawing Sheets

PROCESS FOR THE HYDROFORMYLATION OF OLEFINS

SUMMARY OF THE INVENTION

1. Field of the Invention

The present invention relates to a process for preparing aldehydes and/or alcohols by hydroformylation of olefins or olefin mixtures in the presence of a cobalt catalyst, removal of the catalyst and, if desired, subsequently hydrogenation, with an aldehyde being added to the starting materials in at least one hydroformylation stage. The invention further relates to alcohols and/or aldehydes prepared by the process, and mixtures obtained by the process.

2. Description of the Related Art

Higher aldehydes, in particular those having from 7 to 25 carbon atom can be prepared by catalytic hydroformylation e.d., the oxo process) of the olefins having one fewer carbon atom. The aldehydes are, for example, utilized as precursors in syntheses, for the production of carboxylic acids and as fragrances. In industry, they are often converted by catalytic hydrogenation into the corresponding alcohols which are used, inter alia, as intermediates for the production of plasticizers and detergents.

A large number of processes for the hydroformylation of olefins have been described in the literature. The choice of catalyst system and the optimal reaction conditions for the hydroformylation are dependent on the reactivity of the olefin used. The influence of the structure of the olefin used on its reactivity in hydroformylation is described, for example, by J. FALBE, "*New Syntheses with Carbon Monoxide*", Springer Verlag, 1980, Berlin, Heidelberg, New York, page 95 ff.

A general rule is that the rate of hydroformylation reactions decreases under constant boundary conditions as the number of carbon atoms increases and the degree of branching of the olefin increases. Thus, the reaction rate of linear olefins can exceed that of the branched isomers by more than a power of ten. In addition, the position of the double bond in the olefin has a critical influence on the reactivity. Olefins having a terminal double bond react significantly more quickly than isomers having the double bond in the interior of the molecule. The differing reactivity of isomeric octenes has been studied, for example, by B. L. HAYMORE, A. van HASSELT, R. BECK, *Annals of the New York Acad. Sci.,* 1983, 415, 159–175. A general review and further references are given by B. CORNILS, W. A. HERRMANN, "*Applied Homogeneous Catalysis with Organometallic Compounds*", Vol. 1&2, VCH, Weinheim, N.Y., 1996.

Industrial olefin mixtures used as starting materials for the hydroformylation synthesis often comprise olefin isomers having a wide variety of structures with differing degrees of branching, different positions of the double bond and in some cases olefins having differing molar masses are used. This applies, in particular, to olefin mixtures obtainable by dimerization, trimerization or further oligomerization of olefins having from 2 to 8 carbon atoms or other readily available higher olefins or by cooligomerization of the olefins mentioned. Examples of typical olefin mixtures which are industrially relevant for hydroformylation are tripropene and tetrapropene and also dibutenes, tributenes and tetrabutenes.

In a hydroformylation carried out on an industrial, it is desirable to achieve not only a high conversion but also a high selectivity in order to ensure optimal utilization of the raw material. To achieve a high conversion, a relatively long reaction time and/or relatively high reaction temperatures often have to be accepted in the case of olefins which react slowly. More reactive olefins, on the other hand, can be converted into the aldehydes in a far shorter time under the same reaction conditions. In the joint hydroformylation of mixtures of olefins of differing reactivity, this leads to relatively long reaction times being required to achieve satisfactory conversion even of the olefins which are more difficult to hydroformylate. However, the aldehydes arising from the olefins which react more readily are formed relatively quickly and are then present in the reactor together with the olefins which are more difficult to hydroformylate. This leads to undesirable secondary and subsequent reactions of the aldehydes, e.g. to hydrogenation, to condensation reactions and to the formation of acetals and hemiacetals. It is thus difficult, especially because of the differing reactivity of the olefin isomers, to achieve high conversions and at the same time high selectivities in the hydroformylation.

To keep secondary reactions, in particular those of the aldehyde/aldehydes formed in the hydroformylation, at a low level, the olefin conversions and thus the aldehyde concentrations in the hydroformylation reactor are limited in industrial processes. After the hydroformylation products have been separated off, the unreacted olefins are reacted in the same hydroformylation reactor or one or more further hydroformylation reactor(s).

DE 198 42 371 describes the preparation of alcohols having from 6 to 25 carbon atoms by single-stage hydroformylation of the corresponding olefins and hydrogenation of the hydroformylation products. Here, only part of the olefin fed into the hydroformylation reactor is reacted in a single pass. The liquid output from the reactor is freed of the hydroformylation catalyst and selectively hydrogenated, i.e. the aldehydes are hydrogenated to the corresponding alcohols but the olefins are not hydrogenated. The olefins are separated off by distillation from the output from the selective hydrogenation and are recirculated to the hydroformylation reactor.

Processes for the preparation of higher oxo alcohols in which the hydroformylation is carried out in at least two reactors and the unreacted olefins are separated off from the output from the hydroformylation by distillation and are recirculated to the hydroformylation reactor are described, for example, in DE 100 34 360, DE 198 42 368 and EP 1 057 803.

DE 100 34 360 describes a process for the multistage cobalt- or rhodium-catalyzed hydroformylation of olefins having from 6 to 24 carbon atoms to produce alcohols and/or aldehydes, in which the olefins a) are hydroformylated to a conversion of from 20 to 98% in a hydroformylation step, b) the catalyst is removed from the liquid reactor output obtained in this way, c) the liquid hydroformylation mixture obtained in this way is separated into a low-boiling fraction comprising olefins and paraffins and a bottom fraction comprising aldehydes and/or alcohols, the olefins present in the low-boiling fraction are reacted in further process stages comprising the process steps a, b and c and the bottom fractions of the process steps c) of all process stages are combined.

This process is preferably carried out so that the liquid reactor output from the hydroformylation step a) is a homogeneous liquid phase. The cobalt or rhodium catalysts are preferably used in such a way that they are homogeneously dissolved in the liquid reactor output from the hydroformylation step a).

DE 198 42 368 describes a process for preparing higher oxo alcohols from mixtures of isomeric olefins having from 5 to 24 carbon atoms by two-stage hydroformylation in the presence of a cobalt or rhodium catalyst at elevated temperature and superatmospheric pressure, in which the reaction mixture from the first hydroformylation stage is selectively hydrogenated, the hydrogenation mixture is separated in a distillation into crude alcohol and low boilers comprising predominantly olefins, these are fed to the second hydroformylation stage, the reaction mixture from the second hydroformylation stage is once again selectively hydrogenated, the hydrogenation mixture is separated in a distillation into crude alcohol and low boilers, the crude alcohol is worked up by distillation to give pure alcohol and at least part of the low boilers is taken off to discharge saturated hydrocarbons from the system.

EP 1 057 803 discloses a two-stage process for preparing alcohols from olefins or olefin mixtures. In this process, the feed olefin is hydroformylated to an extent of from 50 to 90% in the presence of a cobalt catalyst in the first reaction stage. After the catalyst has been separated off, the unreacted olefins are separated off by distillation from the reaction output and the olefins which have been separated off are reacted in the second hydroformylation reactor. The hydroformylation products from both stages can be hydrogenated to form the corresponding alcohols. In both reaction stages, the catalyst used is $Co_2(CO)_8$ or $HCo(CO)_4$ which is produced outside the hydroformylation reactors. The cobalt catalyst is removed from the reaction mixture from the hydroformylation by extraction with a base prior to further processing.

In the known processes for the hydroformylation of olefins or olefin mixtures having from 6 to 24 carbon atoms, by-products such as condensation products of the aldehydes, ethers or paraffins are formed despite restriction of the olefin conversion in each hydroformylation reactor.

SUMMARY OF THE INVENTION

Accordingly, it is an object of the present invention to provide a process wherein olefins or olefin mixtures are converted into products of value such as aldehydes, alcohols and their formates in a larger yield than in conventional processes. The products of value can subsequently be hydrogenated to the alcohol(s).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
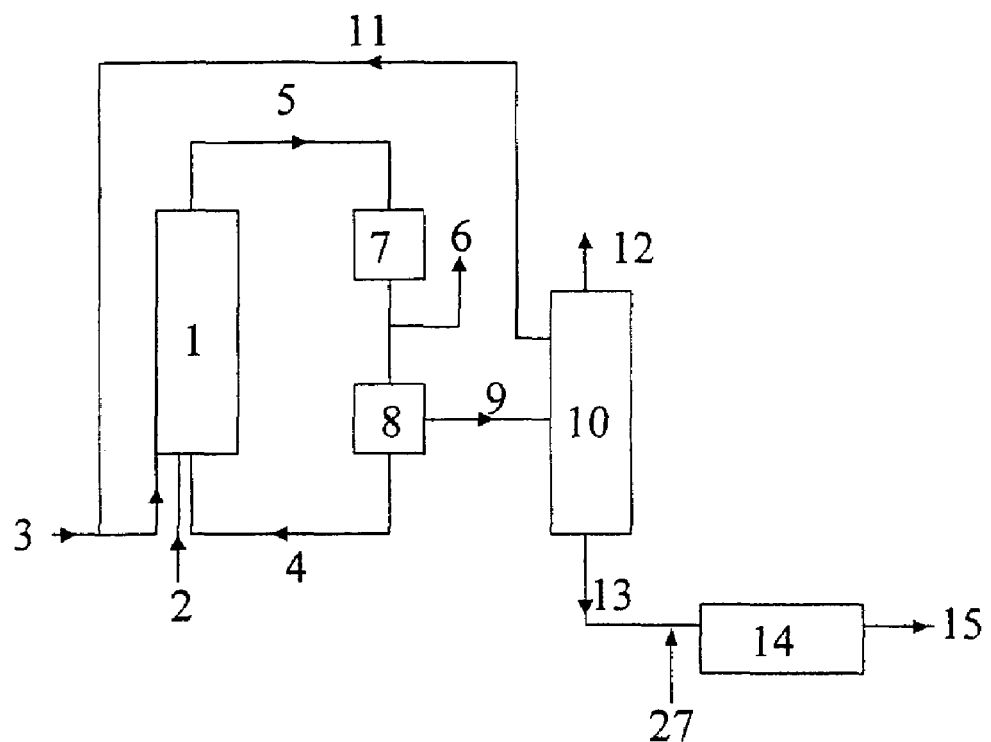
FIG. 1 shows an embodiment of the invention wherein hydroformylation is carried out in a hydroformylation stage in a reactor.

It has now surprisingly been found that the yield of products of value in a single-stage or multistage hydroformylation in which an unmodified cobalt complex acts as catalyst in at least one reactor can be increased if from 0.5 to 20 mol % of aldehyde (i.e. the product of the hydroformylation), based on the olefin fed in, is introduced into this reactor.

This finding is unexpected since, as described above, the selectivity for the formation of products of value decreases with increasing conversion of the olefins and thus increasing aldehyde concentration in the reactor. It would therefore have been expected that the use of a pure olefin or a pure mixture of a plurality of olefins would give a higher selectivity for the formation of products of value than in the case of a starting material containing aldehyde(s) in addition to olefins. It is therefore all the more surprising that the presence of aldehyde(s) in the feed olefin in an amount of from 0.5 to 20 mol %, based on the olefin(s), increases the selectivity of the formation of the desired product in the hydroformylation using an unmodified cobalt complex as catalyst.

The present invention accordingly provides a process for the catalytic hydroformylation of olefins having from 6 to 24 carbon atoms, in which the hydroformylation is carried out in at least one stage, i.e. in one or more stage(s), and a mixture comprising an olefin and an aldehyde having from 7 to 25 carbon atoms in a molar ratio of aldehyde to olefin of from 0.005:1 to 0.2:1 is used as feed in at least one of these stages which is carried out in the presence of an unmodified cobalt complex as catalyst.

The present invention likewise provides a feed mixture which is suitable for use in the process of the invention and comprises at least one olefin having from 6 to 24 carbon atoms and an aldehyde having from 7 to 25 carbon atoms in a molar ratio of aldehyde to olefin of from 0.005:1 to 0.2:1, preferably, from 0.10:1 to 0.1:1.

For the purposes of the present invention, unmodified complexes are metal complexes, in particular of cobalt or of rhodium, whose ligands are selected from among carbon monoxide, hydrogen, olefin, alkyl radicals, alkenyl radicals, acyl radicals and alkoxy radicals, and no compounds containing elements of the fifth main group of the Periodic Table of the Elements (N, P, As, Sb, Bi) are present as ligands.

For the purposes of the present invention, feed mixtures are mixtures which are present in a reactor at the beginning of a reaction or are obtained by introduction into the reactor. The compounds present in the feed mixture can be fed individually or as a mixture into the reactor.

The present invention has the advantage that, in the hydroformylation of higher olefins, the yield can be increased in a simple way and energy may also be able to be saved. The advantage can be utilized both in new plants to be built and also in plants which are already in operation. For example, in an existing hydroformylation plant in which the hydroformylation is carried out in at least two reactors connected in series, the unreacted olefins can be separated off by distillation and fed into the next reactor and the second or subsequent reactor contains an unmodified cobalt complex as catalyst which is generated in the same reactor from an aqueous cobalt salt solution simultaneously with the hydroformylation, an increase in the yield of aldehydes or alcohols can be achieved simply by altering the distillation conditions in the olefin separation column. The desired olefin/aldehyde ratio can be set in the distillate by reducing the reflux ratio. At the same time, the olefin content of the bottom product is reduced. In addition, energy can be saved by the reduction in the reflux ratio. An additional capital investment is not necessary for conversion of existing processes to the process of the invention.

The process is described by way of example below without the invention being restricted to the illustrative embodiments. If ranges, general formulae or classes of compounds are indicated below, these are intended to encompass not only the corresponding ranges or groups of compounds which are explicitly mentioned but also all subranges and subgroups of compounds which can be obtained by omission of individual values (ranges) or compounds.

In the process of the invention for the catalytic hydroformylation of olefins having from 6 to 24 carbon atoms, the hydroformylation is carried out in one or more stages and a mixture comprising at least one olefin, in particular an olefin having from 6 to 24 carbon atoms, and an aldehyde having from 7 to 25 carbon atoms in a molar ratio of aldehyde (or sum of all aldehydes present) to olefin (or sum of all olefins present) of from 0.005:1 to 0.2:1, preferably from 0.01:1 to 0.1:1 and particularly preferably from 0.05:1 to 0.07:1, is used as feed in at least one of these stages which is carried out in the presence of an unmodified cobalt complex as catalyst. The feed mixture particularly preferably comprises aldehydes and olefins, with the olefins having, on average, one carbon atom fewer than the aldehydes. If di-n-butene is hydroformylated, the molar ratio of aldehyde to olefin is preferably in the range from 0.01:1 to 0.07:1. A hydroformylation stage which is carried out in the presence of an unmodified cobalt complex as catalyst and in which a mixture comprising at least one olefin and an aldehyde having from 7 to 25 carbon atoms in a molar ratio of aldehyde to olefin of from 0.005:1 to 0.2:1 is used as feed will hereinafter also be referred to as OA hydroformylation stage.

As aldehyde for producing the feed mixture, any aldehyde having from 7 to 25 carbon atoms can be used. Aldehydes which on average have one carbon atom more than the olefins used are preferably used for producing the feed mixture. Aldehydes which are obtained as product of a hydroformylation, in particular as product of a hydroformylation stage of the process of the invention, are particularly preferably used for producing the feed mixture. The aldehydes used in the respective hydroformylation stage can originate from other hydroformylation stages or else from the same hydroformylation stage.

It is possible to use, for example, a distillate which comprises aldehydes and olefins and has been separated off from a hydroformylation mixture by distillation for producing the feed mixture comprising aldehyde and olefin. However, a hydroformylation mixture or a hydroformylation mixture from which the catalyst has firstly been removed can also be used directly for producing the feed mixture comprising aldehyde and olefin. It is likewise possible to use a distillate which comprises aldehydes and olefins and has been separated off from a hydroformylation mixture and a hydroformylation mixture or a hydroformylation mixture from which the catalyst has firstly been removed (decatalyzed hydroformylation mixture) for producing the feed mixture comprising aldehyde and olefin. The hydroformylation mixtures or the components thereof can in turn originate from any hydroformylation stage in the process. In the case of hydroformylation mixtures which come from a stage operated using a rhodium catalyst, at least the catalyst is firstly separated off from the hydroformylation mixture before it is, after optional further fractionation, used for producing the feed mixture for the OA hydroformylation stage.

The feed mixture having the abovementioned ratios of olefin(s) to aldehyde(s) can be produced, for example, by one of the following possible methods:

1. The work-up of a decatalyzed, olefin-containing hydroformylation mixture by distillation can be set by choice of the distillation conditions so that the low-boiling fraction comprises not only olefins but also aldehydes. Variation of the distillation conditions, in particular the reflux ratio, enables the desired aldehyde/olefin ratio to be set directly. This stream or a part thereof can be used as starting material in an OA hydroformylation stage without addition of olefins and/or aldehydes.

2. By mixing a mixture obtained as in 1 above in suitable ratios with fresh olefin and/or an olefin-containing (low-boiling) fraction which has been obtained from a hydroformylation stage to produce a mixture having the abovementioned ratios of olefin and aldehyde.

3. By mixing a hydroformylation mixture containing an unmodified cobalt complex or a precursor thereof in suitable ratios with fresh olefin and/or an olefin-containing (low-boiling) fraction which has been obtained from a hydroformylation stage and can optionally contain aldehydes to produce a mixture having the abovementioned ratios of olefin and aldehyde.

For the purposes of the present invention, hydroformylation stages are individual hydroformylation reactors or hydroformylation reactors connected in parallel or hydroformylation reactors connected in series in which the starting materials are fed only into the first reactor of the series. The process can be carried out either in only one hydroformylation stage or in two or more hydroformylation stages. If the process is carried out in a plurality of stages, at least part of the hydroformylation product comprising unreacted olefins is, if appropriate after the catalyst has been separated off and/or part or all of the aldehydes have been separated off, in each case fed into the next hydroformylation stage.

It can be advantageous for not only a hydroformylation stage which is carried out in the presence of an unmodified cobalt complex as catalyst and in which a feed mixture comprising at least olefin(s) and aldehyde(s) is used but also at least one further hydroformylation stage in which an unmodified or modified cobalt catalyst or a modified or unmodified rhodium complex is used as catalyst to be present. Use of an additional hydroformylation stage in which a rhodium catalyst is used can be advantageous particularly when the yield of the hydroformylation process is an important aspect, regardless of how large the proportion of terminally hydroformylated products is. If, for example when using the dimerization mixture of n-butenes known as di-n-butene as olefin, an unmodified cobalt catalyst is used in the first stage and an unmodified rhodium catalyst is used in the subsequent stage or stages, the yield is improved while the proportion of terminally hydroformylated products decreases somewhat.

However, it can also be advantageous for cobalt complexes, in particular unmodified cobalt complexes, to be used as catalysts in all hydroformylation stages present in the process of the invention. The exclusive use of cobalt catalysts in processes according to the invention in which more than one hydroformylation stage is present can be advantageous particularly when the product is to have a very high proportion of terminally hydroformylated olefins. Thus, for example when using the mixture of dimerization products of n-butenes known as di-n-butene as olefin, a very high proportion of terminally hydroformylated product is achieved at a satisfactory yield when unmodified cobalt catalysts are used in both stages of a two-stage process.

If exclusively hydroformylation stages or a plurality of hydroformylation stages in which cobalt catalysts are used are present in the process of the invention, it can be particularly advantageous for a mixture comprising at least one olefin and an aldehyde to be used as feed in a plurality of, preferably all, hydroformylation stages in which cobalt complexes are used as catalysts.

The unmodified cobalt complexes used in the hydroformylation stages can be generated simultaneously with the hydroformylation by reaction of an aqueous cobalt salt solution with synthesis gas in the hydroformylation stage or can be previously produced catalysts. Preference is given to using unmodified cobalt catalysts which are generated simultaneously with the hydroformylation by reaction of an aqueous cobalt salt solution with synthesis gas in the hydroformylation stage. Particularly when the hydroformylation is carried out in one stage, an unmodified cobalt complex produced during the hydroformylation, preferably in the same reactor, by reaction of an aqueous cobalt salt solution with synthesis gas is preferably used as catalyst. In processes in which a plurality of hydroformylation stages are present, cobalt and rhodium catalysts with or without complex-stabilizing additives or ligands, e.g. organic phosphines or phosphites, can be used, with the proviso that at least one hydroformylation stage is carried out as an OA hydroformylation stage. Otherwise, the choice of catalyst and reaction conditions (concentration of the catalyst, temperature, pressure, residence time) depends, inter alia, on the number of carbon atoms and the composition of the starting olefins.

In the process of the invention, olefins or mixtures of olefins having from 6 to 24 carbon atoms, preferably from 6 to 20 carbon atoms and particularly preferably from 8 to 20 carbon atoms, can be used as starting materials. The mixtures can comprise olefins having terminal and/or internal C—C double bonds. The mixtures can comprise or consist of olefins having an identical, similar (±2) or significantly different (>±2) number of carbon atoms. Examples of olefins which can be used as feed either in pure form, in a mixture of isomers or in a mixture with further olefins having a different number of carbon atoms are: 1-, 2- or 3-hexene, 1-heptene, linear heptenes having an internal double bond (2-heptene, 3-heptene, etc.), mixtures of linear heptenes, 2- or 3-methyl-1-hexene, 1-octene, linear octenes having an internal double bond, mixtures of linear octenes, 2- or 3-methylheptene, 1-nonene, linear nonenes having an internal double bond, mixtures of linear nonenes, 2-, 3- or 4-methyloctene, 1-, 2-, 3-, 4- or 5-decene, 2-ethyl-1-octene, 1-dodecene, linear dodecenes having an internal double bond, mixtures of linear dodecenes, 1-tetradecene, linear tetradecenes having an internal double bond, mixtures of linear tetradecenes, 1-hexadecene, linear hexadecenes having an internal double bond, mixtures of linear hexadecenes. Further suitable olefins are, inter alia, the mixture of isomeric hexenes obtained in the dimerization of propene (dipropene), the mixture of isomeric octenes obtained in the dimerization of butenes (dibutene), the mixture of isomeric nonenes obtained in the trimerization of propene (tripropene), the mixture of isomeric dodecenes obtained in the tetramerization of propene or the trimerization of butenes (tetrapropene or tributene), the hexadecene mixture obtained in the tetramerization of butenes (tetrabutene) and also olefin mixtures prepared by cooligomerization of olefins having differing numbers of carbon atoms (preferably from 2 to 4), if appropriate after fractional distillation to produce fractions having an identical or similar (±2) number of carbon atoms. Furthermore, it is possible to use olefins or olefin mixtures which have been produced by the Fischer-Tropsch synthesis. Olefins which have been prepared by olefin metathesis or by other industrial processes can also be used. Preferred starting materials are mixtures of isomeric octenes, nonenes, dodecenes or hexadecenes, i.e. oligomers of lower olefins such as n-butenes, isobutene or propene. Other starting materials which are likewise well suited are oligomers of $C_5$-olefins.

There are in principle three process variants for the oligomerization of butenes to produce essentially $C_8$-olefin-containing mixtures. The oligomerization over acid catalysts has long been known, with, for example, zeolites or phosphoric acid on supports being used industrially. This gives isomer mixtures of branched olefins which are essentially dimethylhexenes (WO 92/13818). A process which is likewise practiced worldwide is oligomerization using soluble Ni complexes, known as the Dimersol process (B. CORNILS, W. A. HERMANN, "Applied Homogeneous Catalysis with Organometallic Compounds", Vol. 1&2, VCH, Weinheim, N.Y. 1996). The third process variant is the oligomerization over fixed-bed nickel catalysts; the process has become known in the literature as the Octol process (Hydrocarbon Process., Int. Ed. (1986) 65 (2. Sect. 1) pages 31–33) and is described, for example, in U.S. Pat. No. 5,177,282. For the preparation according to the invention of a $C_9$-alcohol mixture which is suitable, in particular, for the preparation of plasticizers, preference is given to using a $C_8$-olefin mixture which has been obtained from linear butenes by the Octol process.

In the hydroformylation stages, preference is given to using a synthesis gas in which the molar ratio of carbon monoxide to hydrogen is preferably from 1:4 to 4:1, particularly preferably from 1:2 to 2:1, very particularly preferably from 1:1.2 to 1.2:1. In particular, a synthesis gas in which carbon monoxide and hydrogen are present in an approximately stoichiometric ratio is used.

The temperatures and the pressures in the hydroformylation stages of the process of the invention can vary within wide limits depending on the catalyst and olefin mixture. Since the more reactive olefins react preferentially in the first stage of a multistage embodiment of the process, more energetic reaction conditions in respect of temperature, amount of catalyst and residence time are preferably set in the subsequent hydroformylation stages.

The optimal conditions can vary from case to case, depending on the objective: thus, for example, the space-time yield achieved overall, an increase in the selectivity or the desired product properties can be an optimization criterion. In general, the composition of the feed olefin and the choice of catalyst systems and/or the reaction conditions will decide which of the possible embodiments of the process of the invention is optimal from an economic point of view. The optimization can be determined in a suitable way by a person skilled in the art by means of simulation calculations.

The process of the invention is preferably carried out so that, if a plurality of hydroformylation stages are present, conversions of from 20 to 98%, in particular from 40 to 80%, particularly preferably from 50 to 75%, are obtained in the individual hydroformylation stages (in each case in a single pass).

Rhodium- and cobalt-catalyzed hydroformylation processes usually differ in terms of their operating parameters. However, the main difference is the fundamentally different removal and recirculation of the catalyst. The two processes are described separately in more detail below.

Cobalt-catalyzed Hydroformylation

In the process of the invention, an unmodified cobalt complex is used as catalyst in at least one hydroformylation stage. In other stages, unmodified and/or modified cobalt complexes or else rhodium complexes can preferably be used as catalyst. The unmodified cobalt catalysts can be prepared outside the hydroformylation reactor but are preferably generated within the hydroformylation reactor simultaneously with the hydroformylation of the olefins by reaction of an aqueous cobalt salt solution with synthesis gas.

A process in which the unmodified cobalt catalyst e.g., ($HCo(CO)_4$ and/or $Co_2(CO)_4$) is generated in the hydroformylation reactor during the hydroformylation is described, for example, in DE 196 54 340 (incorporated by reference herein in its entirety). In this process which is preferably used as hydroformylation stage in the process of the invention, the starting materials, i.e. a cobalt salt solution, the organic feed mixture and the synthesis gas, are introduced simultaneously, preferably with the aid of a mixing nozzle, in cocurrent from below into the reactor.

As cobalt compounds for preparing the catalyst or the cobalt salt solution, preference is given to using cobalt salts such as formates, acetates or salts of carboxylic acids which are water-soluble. Particular preference is given to using cobalt acetate. The cobalt salts can be used as aqueous solutions which preferably have a cobalt content of from 0.5 to 3% by mass, more preferably from 0.8 to 1.8% by mass, calculated as metal. The cobalt salt solution used can be a freshly prepared solution and/or a cobalt salt solution which is obtained in the removal of the catalyst from the hydroformylation product mixture from a hydroformylation stage.

The amount of water which is wanted in the hydroformylation reactor can be introduced with the cobalt salt solution whose concentration can be varied within a wide range. However, it is also possible to feed in additional water in addition to the cobalt salt solution.

It has been found to be advantageous to attach great importance to the metering of the starting materials into the hydroformylation reactor in the cobalt-catalyzed process. To feed the starting materials into the hydroformylation reactor, the latter should have a metering device which ensures good mixing of the phases and generation of a very high exchange area between the phases. Such a metering device can be, for example, a mixing nozzle. It can also be advantageous to divide the reactor volume of the hydroformylation reactors by installation of from 1 to 10, preferably from 2 to 4, perforated plates arranged perpendicular to the flow direction of the reactant and product stream. This cascading of the reactor greatly reduces backmixing in comparison with a simple bubble column and approximates plug flow behavior. This process engineering measure enables both the yield and the selectivity of the hydroformylation to be improved.

More detailed information on carrying out the cobalt-catalyzed hydroformylation and also specific variants for carrying out the hydroformylation in the hydroformylation stage may be found, for example, in DE 199 39 491 A1 and DE 101 35 906 (each of which is incorporated herein by reference in its entirety). Thus, according to DE 199 39 491, a substream of the liquid mixed phase (aqueous cobalt salt solution/organic phase) is taken off from the lower part of the reactor and is fed back in at a point higher up on the reactor. According to DE 101 35 906, the level of the aqueous phase is kept constant in the hydroformylation reactor, with the concentration of cobalt compounds (calculated as metallic cobalt) in this aqueous bottom phase being in the range from 0.4 to 1.7% by mass.

In another variant of the process of the invention, the finished catalyst is fed in the form of a catalyst solution comprising $Co_2(CO)_8$ dissolved in the feed olefin, or at relatively high temperatures in liquid form, into the hydroformylation reactor. After this catalyst solution has been placed in the reactor, olefin, catalyst, synthesis gas and optionally water and aldehyde are fed into the reactor. Water can be dispersed in the olefin even before the reactor, for example by use of a static mixer. However, it is also possible to mix all components only in the reactor.

The cobalt-catalyzed hydroformylation is preferably carried out at temperatures of from 100 to 250° C., preferably from 140 to 210° C., and/or at a pressure of from 10 to 40 MPa, preferably from 20 to 30 MPa. The volume ratio of carbon monoxide to hydrogen in the synthesis gas used is preferably from 2:1 to 1:2, more preferably from 1.5:1 to 1:1.5 and particularly preferably from 1:1 to 1:1.5. The synthesis gas is preferably used in excess, for example in an amount up to three times the stoichiometric amount based on the olefin. The concentration of cobalt compounds (calculated as metallic cobalt) in the liquid output from the hydroformylation is usually from 0.01 to 0.5% by mass, in particular from 0.02 to 0.08% by mass (based on the sum of organic and aqueous phase).

Due to the different possible ways of adding water, the water content in the input into the hydroformylation reactor can be determined only with difficulty. For this reason, statements are made in the following about the water content of the output from the reactor, with the water content in the output from the reactor being virtually the same as the water content of the liquid phase during the reaction. The water concentration in the liquid hydroformylation outputs from the cobalt-catalyzed hydroformylation stages can be from 0.1 to 10% by mass, in particular from 0.5 to 5% by mass. If a plurality of cobalt-catalyzed hydroformylation stages are present, the water contents of the hydroformylation outputs from the individual stages can be identical or different. The water content is preferably so great that the water is homogeneously dissolved in the liquid hydroformylation outputs.

In the case of processes having a plurality of hydroformylation stages, identical or different conditions can be set in the reactors in which cobalt compounds are used as catalyst. When the process of the invention is carried out in a plurality of hydroformylation stages, particular preference is given to setting a temperature of from 140 to 195° C., preferably from 160 to 185° C., in the first hydroformylation stage, in which the more reactive olefins are reacted. In this process stage, olefin conversions of preferably from 20 to 95%, more preferably from 50 to 80%, are aimed at. In the subsequent hydroformylation stage or stages, in which the less reactive olefins are hydroformylated, the hydroformylation is preferably carried out at temperatures higher than that in the first hydroformylation stage. It is likewise possible to carry out the hydroformylation of the less reactive olefins using a different catalyst, in particular a modified cobalt catalyst or a modified or unmodified rhodium catalyst.

Cobalt Removal

The hydroformylation output from a hydroformylation stage operated using an unmodified cobalt complex as catalyst is, after leaving the hydroformylation reactor, preferably depressurized to a pressure of from 1.0 to 3.0 MPa and separated into a liquid phase and a gaseous phase. The liquid phase is subsequently passed to the actual cobalt removal step. In the cobalt removal step, the liquid phase of the hydroformylation output is reacted with oxygen-containing gases, in particular air or oxygen, at temperatures of from 90 to 160° C. in the presence of acidic, aqueous cobalt(II) salt solutions ("process water") and thus freed of cobalt carbonyl complexes by oxidation. The hydroformylation-active cobalt carbonyl complexes are thus destroyed with formation of cobalt(II) salts. The cobalt removal processes are well known and are comprehensively described in the literature, e.g. by J. FALBE, in "New Syntheses with Carbon Monoxide", Springer Verlag (1980), Berlin, Heidelberg, New York, page 158 ff (incorporated herein by reference in its entirty). The solution used as process water preferably has a pH of from 1.5 to 4.5. The cobalt content of the process water used preferably corresponds almost (deviation less than ±20%, preferably less than ±10% and more preferably less than ±5%) to the cobalt content of the catalyst mixture or catalyst precursor mixture used in the hydroformylation step and is particularly preferably from 0.8 to 2.0% by mass.

The cobalt removal can be carried out in a pressure vessel which is filled with packing elements, e.g. Raschig rings, and in which a very high exchange area for the phases is preferably generated. The product mixture obtained as a result of cobalt removal is separated into an aqueous phase and a virtually cobalt-free organic phase, e.g. in a downstream separation vessel. The aqueous phase, viz. the "process water", which comprises the back-extracted cobalt recovered from the organic phase in the form of cobalt acetate/formate is recirculated in its entirety or after discharge of a small proportion to a hydroformylation stage, preferably to the respective hydroformylation stage, and preferably used as starting material for the in situ preparation of the cobalt catalyst complexes.

Before recirculation of the process water to the hydroformylation reactor, part of the excess formic acid can optionally be removed. This can be achieved, for example, by distillation. Another possibility is to decompose part of the formic acid, for example catalytically as described in DE 100 09 207 (incorporated herein by reference in its entirety).

It is also possible to prepare the actual hydroformylation catalyst (e.g., $Co_2(CO)_8$ and/or $HCo(CO)_4$) from the cobalt salt solution obtained in cobalt removal by precarbonylation and recirculate this to a hydroformylation stage.

The organic phase comprises, inter alia, unreacted olefins, aldehydes, alcohols, formic esters and high boilers and also traces of cobalt compounds. The organic phases which can be obtained from the liquid hydroformylation mixture from one or more hydroformylation stages after removal of the catalyst are preferably passed to a work-up in which the low boilers, preferably the unreacted olefins, are separated from the desired products (aldehyde, alcohol, formates). This work-up is described below.

Work-up

The separation of the olefins from the hydroformylation output is preferably carried out after removal of the catalyst and/or a catalyst phase which may be present and can be effected, for example, by distillation or steam distillation. The distillation is preferably carried out so that an overhead fraction (low-boiling fraction) comprising the unreacted olefins, the paraffins formed by hydrogenation of olefins and dissolved water is obtained. It can be advantageous for at least part of the olefins separated off or of the overhead fraction to be recirculated to one or more hydroformylation stages. If this fraction is to be used as aldehyde-containing fraction for producing the feed mixture or used directly as feed mixture, the distillation conditions have to be selected so that a desired proportion of aldehydes is obtained in the overhead product. These fractions can be introduced either alone or after mixing with an olefin-containing mixture into an OA hydroformylation stage, with this being able to be, for example, a preceding stage, the same stage or a subsequent hydroformylation stage. The subsequent hydroformylation stage can be, in particular, the last hydroformylation stage.

Apart from a work-up in a simple distillation column, it is also possible to carry out the work-up in a distillation column having one or more side offtakes. Fractions comprising aldehydes and olefins can be taken off from the side offtake or offtakes. In this embodiment of the work-up, a fraction which is free or at least virtually free of aldehydes can be obtained as overhead product. Carrying out the work-up in a distillation column having one or more side offtakes thus enables two different olefin-containing fractions to be obtained, as a result of which, particularly if a plurality of hydroformylation stages are present, the flexibility of the use of the olefin-containing fractions increases. Thus, the overhead fraction can, for example, be fed in its entirety or in part to a hydroformylation stage in which a rhodium catalyst is used, while the fraction from the side offtake can be used for producing a feed mixture for an OA hydroformylation stage or directly as feed mixture. It goes without saying that all or part of the overhead fraction can be used for producing a feed mixture.

Rhodium-catalyzed Hydroformylation

If the process of the invention has hydroformylation stages in which modified and/or unmodified rhodium catalysts are used, these hydroformylation stages can be carried out according to the prior art, as is described, for example, in EP 0 213 639, EP 0 214 622, WO 2004/020380 or WO 2004/024661 (each of which is incorporated herein by reference in its entirety). If a plurality of hydroformylation stages in which rhodium catalysts are used are present, the rhodium catalysts used can be identical or different. After the catalyst and a catalyst phase which may be present have been separated off, the further work-up of the hydroformylation mixture can be carried out as described above for the hydroformylation stages which are carried out in the presence of cobalt catalysts.

Hydrogenation

If it is not the aldehyde but the corresponding alcohol which is the actual target compound, the aldehyde can be hydrogenated to form the alcohol. For the purpose of carrying out the hydrogenation, the output from the hydroformylation stage which has preferably been separated from the catalyst and any aqueous phase present can be fed to a hydrogenation stage. Before it is fed to the hydrogenation stage, it can be advantageous also to separate off any olefins still present in the output. This can be effected, for example, by distillation. If the separation is to be dispensed with, the olefins which may be present are either hydrogenated to paraffins in the hydrogenation or else the hydrogenation has to be carried out so selectively that any olefins present are not hydrogenated or hydrogenated to only a small extent (<10%) in the hydrogenation stage.

If a plurality of hydrogenation stages are present in the process of the invention, every stage, only one stage or only some of the stages can have a removal of the olefins and/or a hydrogenation stage. In particular, it can be advantageous for only one removal or only one hydrogenation to be present. In this case, the hydrogenation outputs are collected and fed to a removal and/or a hydrogenation stage. A further possible way of carrying out the hydrogenation in the case of a plurality of hydroformylation stages is to carry out a removal of the olefins and a hydrogenation of the aldehyde fractions in all but the last stage and to hydrogenate the hydroformylation output from the last stage which has been separated from the catalyst and any aqueous phase present directly. The aldehyde fractions can be hydrogenated together in one hydrogenation stage or else in different hydrogenation stages. Particular preference is given to hydrogenating at least part of the hydroformylation mixture from the last hydroformylation stage, preferably after the catalyst and any aqueous phase present have been separated off.

It can be advantageous to separate off small amounts of catalyst residues or their reaction products in a further step prior to the hydrogenation. A method of separating off residues of cobalt compounds by extraction with water is described, for example, in DE 102 27 995 (incorporated herein by reference in its entirety).

The hydrogenation can be carried out using, for example, nickel, copper, copper/nickel, copper/chromium, copper/chromium/nickel, zinc/chromium or nickel/molybdenum catalysts. The catalysts can be unsupported or the hydrogenation-active substances or their precursors can have been applied to supports, for example silicon dioxide or aluminum oxide.

Preferred catalysts over which the hydroformylation mixtures are hydrogenated comprise from 0.3 to 15% by mass of each of copper and nickel and also, as activators, from 0.05 to 3.5% by mass of chromium and advantageously from 0.01 to 1.6% by mass, preferably from 0.02 to 1.2% by mass, of an alkali component on a support material, preferably aluminum oxide and silicon dioxide. The amounts indicated are based on the not yet reduced catalyst. The alkali component is optional. This catalyst is suitable, in particular, as catalyst for the selective hydrogenation of the aldehydes. Further details regarding the selective hydrogenation may be found in DE 198 42 370 (incorporated herein by reference in its entirety).

The catalysts are preferably used in a form in which they offer a low flow resistance, e.g. in the form of granules, pellets or shaped bodies such as tablets, cylinders, rod extrudates or rings. They are preferably activated, e.g. by heating in a stream of hydrogen, before use.

The hydrogenation is preferably carried out as a liquid-phase hydrogenation. The hydrogenation is preferably carried out at a total pressure of from 0.5 to 50 MPa, particularly preferably at a pressure of from 1.5 to 10 MPa. A hydrogenation in the gas phase can also be carried out at lower pressures, with correspondingly large gas volumes. If a plurality of hydrogenation reactors are used, the total pressures in the individual reactors can be identical or different within the specified pressure limits.

The reaction temperatures in the hydrogenation in the liquid or gaseous phase are preferably in the range from 120 to 220° C., more preferably from 140 to 180° C. Examples of hydrogenations which can be used in the hydrogenation stage are described, for example, in the patent applications DE 198 42 369 and DE 198 42 370 (incorporated herein by reference in its entirety). The hydrogenation can optionally be carried out with addition of water. A liquid-phase process for the hydrogenation of hydroformylation mixtures in the presence of water is disclosed, for example, in DE 102 41 266 (incorporated herein by reference in its entirety).

The output from the hydrogenation stage or stages can be worked up to produce pure alcohol in one or more distillations.

The process of the invention can be carried out batchwise or preferably continuously.

Some process variants of the process of the invention, including some process variants for the multistage hydroformylation presented by way of example as a two-stage process, are described below. However, it should be emphasized that the ways of carrying out the process which are described here also apply analogously to processes having more than two hydroformylation stages. Furthermore, the embodiments of the process of the invention which are described below by way of example should not be regarded as a restriction of the process of the invention to these embodiments.

Embodiment 1

One variant of embodiment 1 of the process of the invention is shown in the form of a block diagram in FIG. 1. In this variant, the hydroformylation is carried out in one hydroformylation stage in a reactor. The catalyst is an unmodified cobalt complex which is generated simultaneously with the hydroformylation by reaction of an aqueous cobalt salt solution with synthesis gas. The feed olefin (mixture) 3, recycle olefin 11, synthesis gas (carbon monoxide and hydrogen) 2 and an aqueous solution of a cobalt compound 4 are fed into the hydroformylation reactor 1. The hydroformylation mixture 5 obtained in this way is depressurized to from 1.5 to 3.0 MPa and, after the cobalt removal 7 carried out using water and air, is freed of cobalt solution 4 in the catalyst separation 8. Prior to the catalyst separation 8, excess synthesis gas 6 is taken off. The aqueous phase 4 containing cobalt salts is recirculated to the hydroformylation reactor 1, if appropriate after discharge of a small substream and replacement by fresh catalyst. For the present purposes, the term catalyst includes precursors of catalysts, e.g. cobalt(II) salt solutions. The organic phase 9 which has been freed of the catalyst is separated in a separation stage 10 into a low-boiling fraction 11 comprising olefin and aldehydes, a virtually aldehyde-free fraction 12 which is discharged to separate off paraffins and other low-boiling by-products, and crude aldehyde 13. The crude aldehyde 13 can be hydrogenated by means of hydrogen 27 in the hydrogenation unit 14 to give the corresponding alcohols 15 which can be worked up to produce pure alcohol in a distillation unit (not shown).

Embodiment 2

In this embodiment of the process of the invention, too, the hydroformylation is carried out in only one hydroformylation stage in a reactor. The catalyst is once again generated in the hydroformylation reactor simultaneously with the hydroformylation by reaction of synthesis gas with an aqueous cobalt salt solution. Embodiment 2 differs from embodiment 1 in that the desired amount of aldehyde is introduced entirely or partly by recirculation of part of the liquid hydroformylation output.

Figure 2:
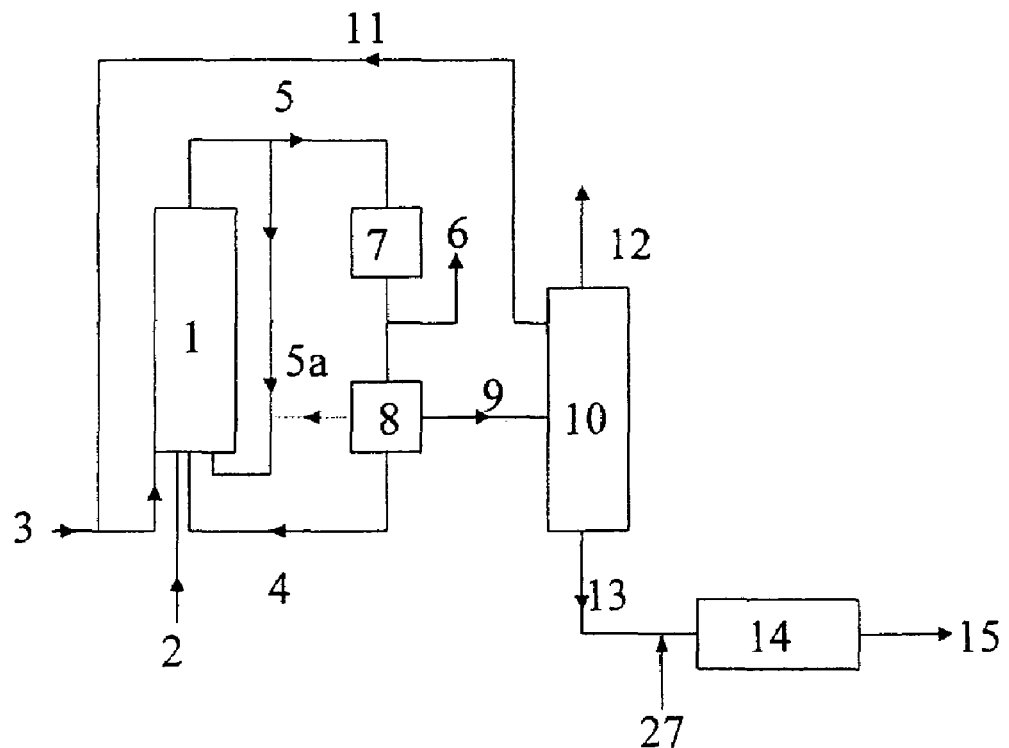
FIG. 2 shows an embodiment of the invention process in the form of a blocked diagram wherein a feed olefin, synthesis and aqueous solution of a catalyst are fed into a hydroformylation reactor.

One variant of embodiment 2 of the process of the invention is shown in the form of a block diagram in FIG. 2. The feed olefin (mixture) 3, if appropriate recycle olefin 11, synthesis gas (carbon monoxide and hydrogen) 2, an aqueous solution of a cobalt compound 4 and hydroformylation output 5a, with or without catalyst, are fed into the hydroformylation reactor 1. The hydroformylation mixture 5 obtained in this way is depressurized to from 1.5 to 3 MPa and, after the cobalt removal 7 carried out using water and air, is freed of cobalt compounds 4 in the first catalyst separation 8. Prior to the catalyst separation 8, excess synthesis gas 6 is taken off. The aqueous phase 4 containing cobalt salts is recirculated to the first hydroformylation reactor 1, if appropriate after discharge of a small substream and replacement by fresh catalyst. For the present purposes, the term catalyst includes precursors of catalysts, e.g. cobalt(II) salt solutions. The organic phase 9 which has been freed of the catalyst is separated in a separation stage 10 into a hydrocarbon fraction 11 comprising olefin and optionally aldehydes, a virtually aldehyde-free fraction 12 which is discharged to separate off paraffins and other low-boiling by-products, and crude aldehyde 13. If no aldehyde is recirculated to the reactor in the distillate, stream 11 and 12 can optionally be taken off as one stream from which a purge stream is separated off. The crude aldehyde 13 can be hydrogenated by means of hydrogen 27 in the hydrogenation unit 14 to give the corresponding alcohols which can be worked up to produce pure alcohol in a distillation unit (not shown).

Embodiment 3

In the illustrative embodiment 3, the process is carried out using two hydroformylation stages which each have one hydroformylation reactor, with an unmodified cobalt complex, which can be generated simultaneously with the hydroformylation by reaction of an aqueous cobalt salt solution with synthesis gas, being used as catalyst at least in the second hydroformylation reactor.

Figure 3:
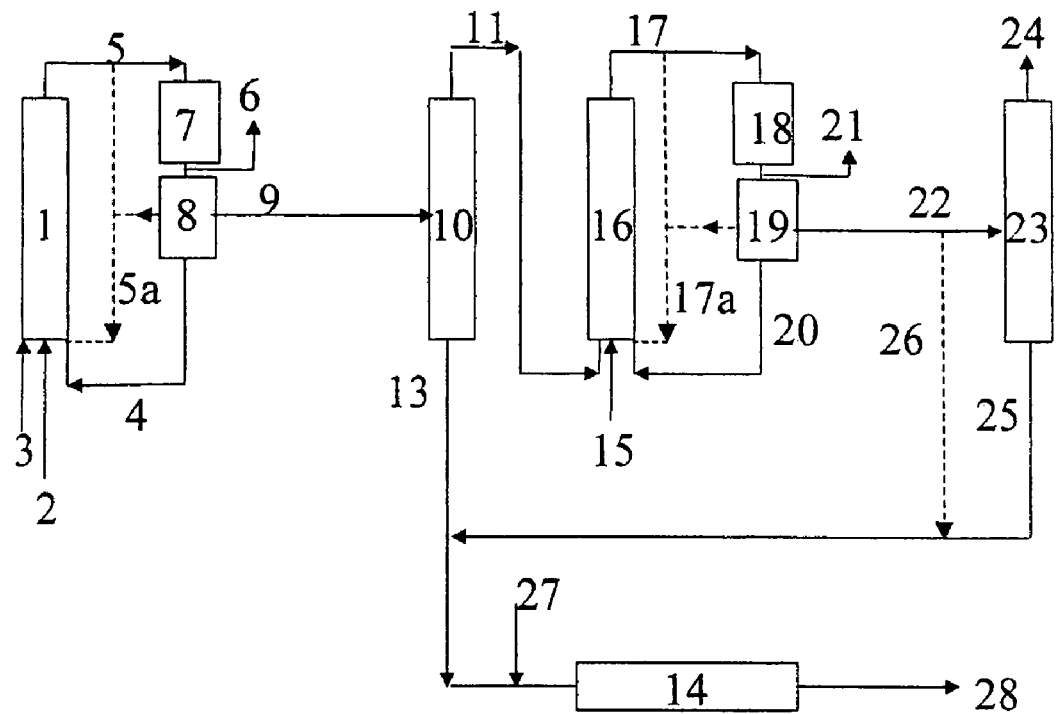
FIG. 3 shows an embodiment of the invention process carried out using two hydroformylation stages.

One variant of embodiment 3 of the process of the invention is shown in the form of a block diagram in FIG. 3. The olefin mixture 3, the synthesis gas 2 (carbon monoxide and hydrogen) and a catalyst solution 4 are fed into the first hydroformylation reactor 1. The hydroformylation mixture 5 obtained in this way is depressurized and, after the cobalt removal 7 carried out using water and air, is freed of cobalt compounds 4 in the first catalyst separation 8. Prior to the catalyst separation 8, excess synthesis gas 6 is taken off. The catalyst-containing phase 4 is recirculated to the first hydroformylation reactor 1, if appropriate after discharge of a small substream and replacement by fresh catalyst. For the present purposes, the term catalyst includes precursors of catalysts, e.g. cobalt(II) salt solutions. The organic phase 9 which has been freed of the catalyst is separated in a separation stage 10 into a low-boiling fraction 11 consisting predominantly of unreacted olefins and aldehydes in the desired ratio, and crude aldehyde 13. The low boilers 11, synthesis gas 15 and an aqueous solution of a cobalt compound 20 are introduced into the second hydroformylation reactor 16. The hydroformylation reactor 17 from the second hydroformylation reactor 16 is depressurized to from 1.5 to 3 MPa and, after the cobalt removal 18 carried out using water and air, freed of the catalyst 20 in the second catalyst separation 19. Prior to the catalyst separation 19, excess synthesis gas 21 is taken off. The catalyst 20 which has been separated off is recirculated to the second hydroformylation reactor 16, if appropriate after discharge of a small substream and replacement by fresh catalyst. The decatalyzed hydroformylation mixture 22 can be fractionated in the separation stage 23 to give a low-boiling fraction 24, which consists predominantly of saturated hydrocarbons, and crude aldehyde 25. If appropriate, part of the low-boiling fraction 24 can be fed back into one of the reactors 16 or 1. (Lines not shown in FIG. 3.) The aldehyde-containing fractions 13 and 25 can be fed either individually or, as shown in FIG. 3, together to a hydrogenation 14 in which the aldehydes are hydrogenated by means of hydrogen 27 to give alcohols 28 which can optionally be worked up to produce pure alcohol in a distillation (not shown).

In a further variant of this embodiment, the hydroformylation mixture 22 from which the cobalt has been removed is, without fractionation in the separation stage 23, fed together with the crude aldehyde 13 from the first hydroformylation stage into the hydrogenation unit 14 (line 26).

In embodiment 3, aldehyde can optionally be fed into the second hydroformylation reactor 16 by recirculation of catalyst-free or catalyst-containing hydroformylation output 17a from the second hydroformylation reactor 16. In the limiting case, the desired amount of aldehyde can be introduced into the second reactor 16 via stream 17a, so that the stream 11 contains virtually no aldehyde or does not have to contain any appreciable amount of aldehyde.

If an unmodified cobalt complex which is generated in the hydroformylation reactor simultaneously with the hydroformylation by reaction of an aqueous cobalt salt solution with synthesis gas is used as catalyst in the first reactor, too, it can be advantageous to recirculate part of the catalyst-free or catalyst-containing hydroformylation output 5a to the first hydroformylation reactor 1. It could likewise be advantageous to recirculate part of the aldehyde-containing stream 11 (via a line which is not shown) to the first hydroformylation reactor.

Embodiment 4

In a further embodiment 4 of the process of the invention, two hydroformylation stages are likewise present, and once again an unmodified cobalt complex which can be generated simultaneously with the hydroformylation by reaction of an aqueous cobalt salt solution with synthesis gas is used at least in the second hydroformylation reactor. The catalyst for the first reactor can be chosen freely. The main difference from embodiment 3 is that the two decatalyzed hydroformylation outputs are worked up together.

Figure 4:
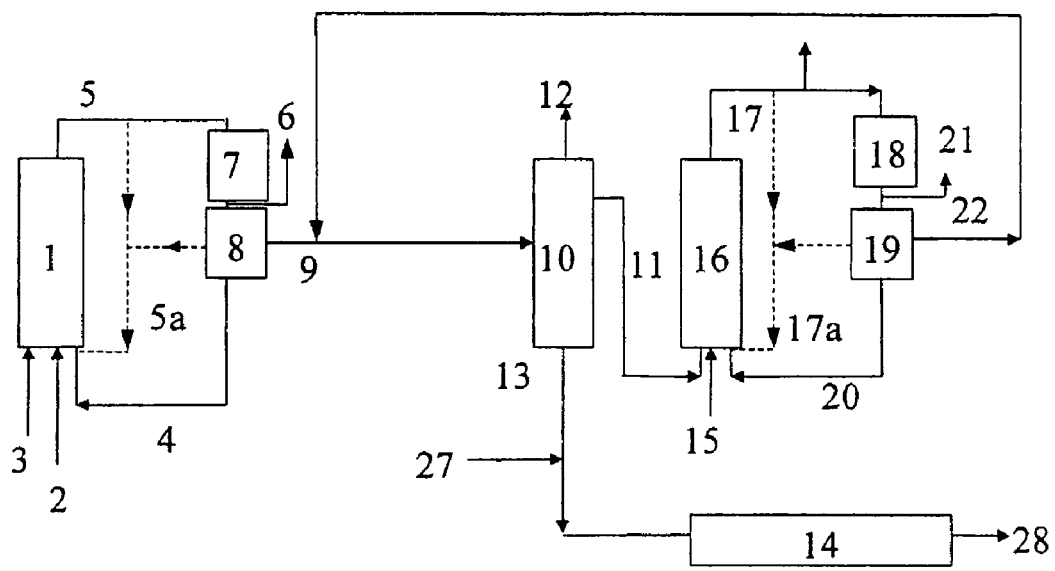
FIG. 4 shows a blocked diagram of another embodiment of the invention wherein an olefin mixture, a synthesis gas and a catalyst solution are fed into a first hydroformylation reactor.

FIG. 4 shows a block diagram of a variant of embodiment 4 of the process of the invention. The olefin mixture 3, the synthesis gas 2 (carbon monoxide and hydrogen) and a catalyst solution 4 are fed into the first hydroformylation reactor 1. The hydroformylation mixture 5 obtained in this way is depressurized and, after the cobalt removal 7 carried out using water and air, is freed of cobalt compounds 4 in the first catalyst separation 8. Prior to the catalyst separation 8, excess synthesis gas 6 is taken off. The catalyst-containing phase 4 is recirculated to the first hydroformylation reactor 1, if appropriate after discharge of a small substream and replacement by fresh catalyst. For the present purposes, the term catalyst includes precursors of catalysts, e.g. cobalt(II) salt solutions. The decatalyzed organic phase 9 is introduced into the separation stage 10. There, it is separated together with the decobalted hydroformylation mixture 22 from the second hydroformylation reactor 16 into a fraction 11 comprising the unreacted olefins and aldehyde, a low-boiling fraction 12 in which paraffins and other low boilers are concentrated and crude aldehyde 13. The low-boiling fraction 12 is discharged. The hydrocarbon fraction 11 is fed together with synthesis gas 15 and an aqueous solution of a cobalt compound 20 into the second hydroformylation reactor 16. The hydroformylation mixture 17 is depressurized and, after the cobalt removal 18 carried out using water and air, is freed of the catalyst 20 in a second catalyst separation 19. Prior to the catalyst separation 19, the excess synthesis gas 21 is taken off. The catalyst 20 which has been separated off is recirculated to the second hydroformylation reactor 16, if appropriate after discharge of a small substream and replacement by fresh catalyst. The second hydroformylation mixture 22 from which the cobalt has been removed is fed together with the hydroformylation mixture 9 from the first stage, as already mentioned, into the separation stage 10. The crude aldehyde 13 can be hydrogenated by means of hydrogen 27 in the hydrogenation unit 14 to give the crude alcohol 28. This alcohol can be worked up to produce the pure alcohol in a distillation (not shown).

In embodiment 4, aldehyde can optionally be fed into the second hydroformylation reactor 16 by recirculation of catalyst-free or catalyst-containing hydroformylation output (lines 17a shown as broken lines) from the second hydroformylation reactor 16. In the limiting case, the desired amount of aldehyde can be introduced into the second reactor 16 via stream 17a, so that the stream 11 need not contain any appreciable amount of aldehyde.

If an unmodified cobalt complex which is generated in the hydroformylation reactor simultaneously with the hydroformylation by reaction of an aqueous cobalt salt solution with synthesis gas is used as catalyst in the first reactor, too, it can be advantageous to recirculate part of the catalyst-free or catalyst-containing hydroformylation output (lines 5a shown as dotted lines) to the first hydroformylation reactor 1. It could likewise be advantageous to recirculate part of the aldehyde-containing stream 11 (via a line which is not shown) to the first hydroformylation reactor.

Embodiment 5

The embodiment 5 of the process of the invention which is described below is likewise carried out using two hydroformylation stages. Unmodified cobalt complexes function as catalyst in both reactors. In at least one reactor, in particular in the second reactor, the catalyst is generated during the hydroformylation by reaction of an aqueous cobalt salt solution with synthesis gas. In a very particularly preferred embodiment of this variant, the active cobalt complex is prepared during the hydroformylation by reaction of a cobalt salt solution with synthesis gas in both reactors.

Figure 5:
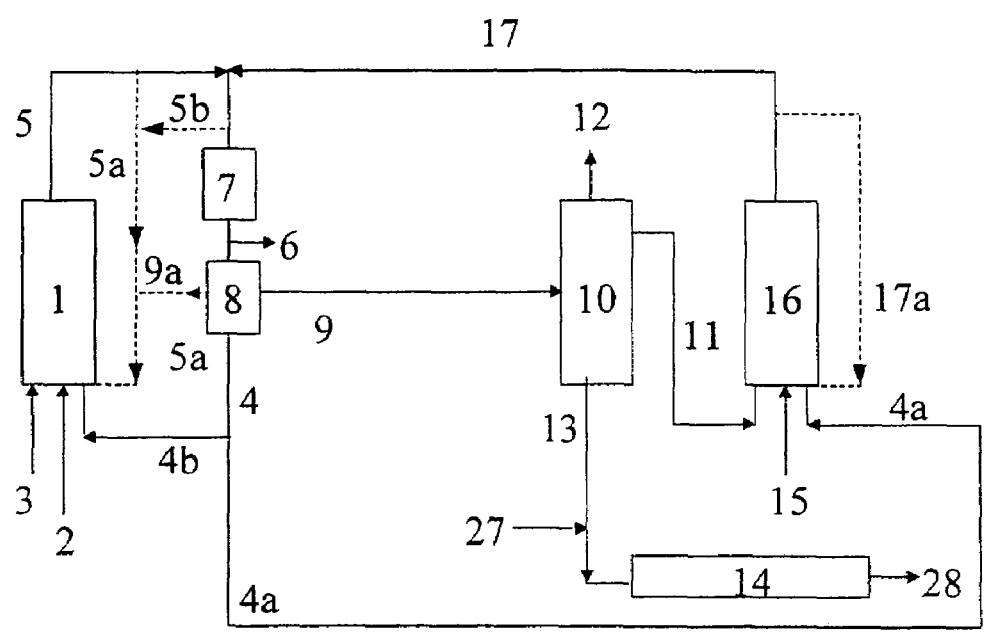
FIG. 5 shows a block diagram of a variant of the process of the invention.

A block diagram of one variant of the embodiment 5 of the process of the invention is shown in FIG. 5. The olefin mixture 3, the synthesis gas 2 (carbon monoxide and hydrogen) and an aqueous solution of a cobalt compound 4b are fed into the first hydroformylation reactor 1. The hydroformylation mixture 5 obtained in this way is depressurized together with the hydroformylation mixture 17 from the second hydroformylation reactor 16 as combined hydroformylation outputs to preferably from 1.5 to 3.0 MPa and, after the cobalt removal 7 carried out using water and air, is freed of the catalyst 4 in the catalyst separation 8. Prior to the catalyst separation 8, the excess synthesis gas 6 is taken off. This gives a mixture 9 comprising the aldehydes formed, alcohols and unreacted olefins. The catalyst 4 is, if appropriate after discharge of a proportion and replacement by fresh catalyst, divided into the two substreams 4b and 4a. Substream 4b is recirculated to the first hydroformylation reactor 1 and substream 4a is recirculated to the second hydroformylation reactor 16. The hydroformylation output 9 from which the cobalt has been removed is fractionated in the separation stage 10 to give the fraction 11 comprising mainly olefins and aldehydes, a virtually aldehyde-free low-boiling fraction 12 in which paraffins and other low-boiling by-products are concentrated and the crude aldehyde 13. The low-boiling fraction 12 is discharged. The fraction 11 is introduced together with synthesis gas 15 and an aqueous solution of a cobalt compound 4a into the second hydroformylation reactor 16. The crude aldehyde 13 can be hydrogenated by means of hydrogen 27 in the hydrogenation unit 14 to give the crude alcohol 28. This can once again be worked up to produce pure alcohol in a distillation (not shown).

In variant 5, aldehyde can optionally be introduced into the second hydroformylation reactor 16 by introduction of catalyst-containing hydroformylation output 17a from the second reactor 16, by introduction of a catalyst-containing mixture from both reactors (line not shown, taken off upstream of or in the apparatus 7) or by introduction of the decatalyzed mixture 9 from both reactors (line not shown) or by introduction of two or three of these streams. In the limiting case, the desired amount of aldehyde can be introduced into the second reactor 16 via this stream/these streams, so that stream 11 need not contain any appreciable amount of aldehyde.

The catalyst-containing hydroformylation mixture 5a from the first reactor 1, the catalyst-containing mixture 5b of the hydroformylation outputs from both reactors or the decatalyzed mixture 9a of the two hydroformylation outputs or any combination of these streams can optionally be introduced into the first reactor 1 in order to set a particular olefin/aldehyde ratio in the inflow into the first reactor. It could likewise be advantageous to introduce part of the aldehyde-containing stream 11 (through a line which is not shown) into the first hydroformylation reactor 1.

The present invention is described by way of example in the following examples, without the invention, whose scope is defined by the description and the claims, being restricted to the embodiments presented in the examples.

EXAMPLE 1

Continuous 2-Stage Process, 1st Hydroformylation Stage

A hydroformylation of olefins was carried out continuously in an experimental plant consisting essentially of a vertical high-pressure tube reactor (diameter: 90 mm, length: 3600 mm) and a downstream cobalt removal vessel (capacity: 5 l) filled with Raschig rings and also a phase separation vessel (capacity: 30 l). The reactor volume of the high-pressure reactor was cascaded by means of a plurality of perforated plates installed orthogonally to the flow direction (5 perforated plates, the first at a height of 1000 mm on the reactor, the remainder spaced at 500 mm intervals). A 3-fluid mixing nozzle was used for introducing the starting materials at the bottom end of the reactor. The contents of the reactor could be heated or cooled as required via the installed heating and cooling facilities.

Before the beginning of the hydroformylation, 15 l of di-n-butene (from the Octol process of OXENO Olefinchemie GmbH) and 3 l of aqueous cobalt acetate solution (1% by mass of cobalt) were introduced into the reactor. After the reactor had been brought to the operating temperature of 175–185° C., the further starting materials, viz. $C_8$-olefin (di-n-butene from the OXENO Octol process), aqueous cobalt acetate solution containing 1% by mass of cobalt and the synthesis gas (volume ratio of CO $H_2$=1:1) were fed continuously into the reactor via the mixing nozzle.

The following throughputs were set: 10.0 kg/h of di-n-butene and 0.50 kg/h of Co acetate solution. The reactor was maintained at a constant reaction pressure of 27 MPa at a synthesis gas throughput of from 5.0 to 9.5 standard $m^3$/h by means of synthesis gas. After a running time of 5 hours, steady-state operation had been achieved. The organic phase was continuously taken off at the top of the reactor, depressurized to from 1 to 1.5 MPa and subsequently introduced into the cobalt removal vessel. Process water (8 kg/h) was added to the organic phase upstream of the cobalt removal vessel.

In the cobalt removal stage, the now two-stage mixture was freed of Co-carbonyl complexes at 140° C. by means of 25 standard l/h of air in the presence of process water by conversion into cobalt acetate and/or cobalt formate and was subsequently separated in a downstream separation vessel. The largely cobalt-free organic phase was freed of unreacted $C_8$-olefins by distillation (see Examples 2 and 3).

Di-n-butene conversions of about 80% were achieved under the reaction conditions selected. The crude product mixture after cobalt removal had, according to GC analysis, the following composition in % by mass: 19.8% of $C_8$-hydrocarbons of which 4.6% were $C_8$-paraffins, 57.6% of isononanals, 18.3% of isononanols, 2.7% of esters (isononyl formates) and 1.6% of residue. After the cobalt removal, the $C_8$-hydrocarbons in the crude product were separated off from desired products (isononanal, isononanol and isononyl formates) in a subsequent distillation. The $C_8$-olefin-containing hydrocarbons were used as feed in the second oxo stage.

EXAMPLES 2 AND 3

Separation of $C_8$-hydrocarbons from Desired Products by Distillation

With the aim of separating $C_8$-hydrocarbons (olefins and paraffins) from the desired products, about 250 kg in each case of a reaction product (product of the cobalt removal stage) from Example 1 were distilled batchwise in two experiments in a distillation column.

The distillation experiments were carried out using a batch column which had a diameter of 80 mm and was packed with 5 m of Sulzer DX laboratory packing.

EXAMPLE 2

Not According to the Invention

In a first distillation experiment at a temperature at the top of 67° C., a pressure of 0.01 MPa and a reflux ratio of 5, a virtually $C_9$-aldehyde-free $C_8$-hydrocarbon fraction (46 kg) was taken off overhead as low boiler. According to GC analysis, this fraction comprised 99.9% by mass of residual $C_8$-hydrocarbons (76.9% by mass of $C_8$-olefins, 23.0% by mass of $C_8$-paraffins) and 0.1% by mass of $C_9$-aldehydes. The bottom fraction (197 kg) comprised $C_9$-aldehydes, $C_9$-alcohols and isononyl formates as desired products. The following composition of the bottom fraction was determined by GC analysis: 71.7% by mass of isononanals, 22.7% by mass of isononanols, 3.4% by mass of esters (isononyl formates), 2.0% by mass of high boilers and 0.2% by mass of $C_8$-hydrocarbons. The $C_8$-olefin-containing overhead fraction was used as feed for the hydroformylation in the second oxo stage (see Example 4).

EXAMPLE 3

According to the Invention

In the distillation of the second 250 kg of the product from the cobalt removal stage, higher contents of $C_9$-aldehyde (isononanols) were deliberately permitted in the $C_8$-hydrocarbon fraction by choice of appropriate distillation conditions (temperature at the top: 70° C., pressure: 0.01 MPa, and reflux ratio of 2). The fraction of about 45.5 kg taken off overhead as low boiler comprised 95.0% by mass of $C_8$-hydrocarbons together with about 5.0% by mass of isononanals. The $C_8$-olefin-containing overhead fraction is used as feed for the hydroformylation in the second hydroformylation stage (see Example 5). The bottom fraction (196 kg) was found to have the following composition by GC analysis: 71.5% by mass of isononanals (INA), 23.0% by mass of isononanols, 3.3% by mass of esters (isononyl formates), 2.0% by mass of high boilers and 0.2% by mass of $C_8$-hydrocarbons.

EXAMPLE 4

(Not According to the Invention) 2nd Hydroformylation Stage Using INA-free $C_8$-olefins The hydroformylation of the olefins obtained by distillation in Example 2 was carried out continuously in an experimental plant as in Example 1. The residual $C_8$-hydrocarbons from the first oxo stage which were used as feed comprised 77% by mass of $C_8$-olefins together with about 23% by mass of $C_8$-paraffins which had been formed by undesired hydrogenation of the $C_8$-olefins in the first hydroformylation stage. After the reactor had been brought to the operating temperature of 180–195° C., the starting materials, viz. the residual $C_8$-hydrocarbons, the aqueous cobalt acetate solution containing 1% by mass of Co and the synthesis gas (volume ratio of $CO/H_2=1:1$), were fed continuously into the reactor via the mixing nozzle. Before the beginning of the hydroformylation, the residual $C_8$-hydrocarbons and cobalt acetate solution are placed in the reactor (for amounts, see Example 1).

The following throughputs were set: 5.0 kg/h of $C_8$-hydrocarbon mixture and 0.35 kg/h of Co acetate solution. The reactor was maintained at a constant reaction pressure of 27 MPa at a synthesis gas throughput of from 2.5 to 5.5 standard m$^3$/h by means of synthesis gas. The organic phase is continuously taken off at the top of the reactor (7.4 kg/h) and depressurized into the cobalt removal vessel to from 1.0 to 1.5 MPa. 4 kg/h of process water were added to the organic phase upstream of the cobalt removal vessel.

In the cobalt removal stage, the two-phase mixture now present in the vessel is reacted at 140° C. in the presence of 15 standard l/h of air and the organic phase is freed of Co-carbonyl complexes by reaction to form cobalt acetate and is subsequently separated from the aqueous phase in a downstream separation vessel. The largely cobalt-free organic phase was analyzed. The crude product mixture after cobalt removal had, according to GC analysis, the following composition in % by mass: 29.3% of $C_8$-hydrocarbons (6.9% of $C_8$-olefins, 22.4% of $C_8$-paraffins), 23.3% of isononanals, 36.9% of isononanols and 5.3% of esters (isononyl formates) and also 5.2% of residue. Under the reaction conditions selected, $C_8$-olefin conversions of about 88.8% and desired product yields of 81.9% were achieved.

EXAMPLE 5

(According to the Invention) 2nd Hydroformylation Stage Using INA-containing $C_8$-olefins The hydroformylation of the olefins obtained by distillation in Example 3 is carried out continuously in an experimental plant as described in Example 4. The residual $C_8$-hydrocarbons used as feed (overhead fraction from Example 3) comprised 73.18% by mass of $C_8$-olefins and 21.86% by mass of $C_8$-paraffins together with 4.96% by mass of C9-aldehydes.

After the reactor had been brought to the operating temperature of 180–195° C., the starting materials, viz. the residual $C_8$-hydrocarbons, the aqueous cobalt acetate solution containing 1% by weight of Co and the synthesis gas (volume ratio of $CO/H_2$=1:1), were fed continuously into the reactor via the mixing nozzle.

The following throughputs were set: 5.28 kg/h of distillate from Example 3 and 0.35 kg/h of Co acetate solution. The reactor was maintained at a constant reaction pressure of 27 MPa at a synthesis gas throughput of from 2.5 to 5.5 standard $m^3$/h by means of synthesis gas. The organic phase was taken off continuously at the top of the reactor (7.6 kg/h) and depressurized into the cobalt removal vessel to from 1.0 to 1.5 MPa. 4 kg/h of process water were added to the organic phase upstream of the cobalt removal vessel. In the cobalt removal stage, the organic phase is freed of Co-carbonyl complexes at 140° C. in the presence of 16 standard l/h of air by reaction to form cobalt acetate and/or cobalt formate and is subsequently separated from the aqueous phase in a downstream separation vessel.

The largely cobalt-free organic phase comprising the desired products was analyzed. The amount of isononanal introduced into the reactor via the feed were taken into account in the evaluation of the analytical results (calculation of conversion and yield). The crude product mixture after cobalt removal had, according to GC analysis, the following composition in % by mass: 26.3% of $C_8$-hydrocarbons (5.2% of $C_8$-olefins, 21.1% of $C_8$-paraffins), 20.8% of isononanals, 41.9% of isononanols and 5.4% of esters (isononyl formates) and also 5.6% of residue. Under the reaction conditions selected, $C_8$-olefin conversions of about 91.7% and yields of desired products of 84.3% were achieved.

A comparison of the $C_8$-olefin conversions and yields in the hydroformylation of $C_8$-olefins with (Example 5) and without isononanal (Example 4) in the feed showed that an appreciable improvement in the conversions and yields is achieved by use of a $C_9$-aldehyde-containing feed. According to the present results, use of the process of the invention in the second hydroformylation stage was able to increase the conversion by about 2.9 percentage points and the yield by about 2.4 percentage points compared to processes of the prior art.

German application 10 2004 059293.4 filed on Sep. 12, 2004 is incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

The invention claimed is:

1. A process for catalytically hydroformylating one or more olefins having from 6 to 24 carbon atoms, comprising:
   hydroformylating, in one or more stages, one or more olefins having from 6 to 24 carbon atoms; while
   feeding a mixture comprising an olefin and one or more aldehydes having from 7 to 25 carbon atoms to at least one stage in which the hydroformylating is carried out;
   wherein the hydroformylating is carried out in the presence of an unmodified cobalt complex, and wherein the molar ratio of the aldehyde to the olefin in the mixture is from 0.005:1 to 0.2:1.

2. The process as claimed in claim 1, wherein the molar ratio of aldehyde to olefin present in the mixture is from 0.01:1 to 0.07:1.

3. The process as claimed in claim 1, wherein the hydroformylating is carried out in one stage.

4. The process as claimed in claim 1, wherein the hydroformylating is carried out in at least two stages.

5. The process as claimed in claim 4, comprising:
   carrying out the hydroformylating in at least one stage in the presence of a modified or unmodified rhodium complex.

6. The process as claimed in claim 4, comprising:
   carrying out the hydroformylating in the presence of a cobalt complex in all of the stages.

7. The process as claimed in claim 6, wherein the cobalt complex in all of the hydroformylating stages is an unmodified cobalt complex.

8. The process as claimed in claim 6, comprising:
   feeding the mixture comprising at least one olefin and at least one aldehyde to each of the hydroformylating stages wherein hydroformylating is carried out in the presence of a cobalt complex.

9. The process as claimed in claim 1, further comprising:
   generating the unmodified cobalt complex during the hydroformylating by reacting an aqueous cobalt salt solution with a synthesis gas present during the hydroformylating.

10. The process as claimed in claim 1, wherein a distillate which comprises aldehydes and olefins and has been separated off from a hydroformylation mixture is used for producing the feed mixture of aldehyde and olefin or directly as feed mixture.

11. The process as claimed in claim 1, wherein a hydroformylation mixture is used for producing the feed mixture of aldehyde and olefin.

12. The process as claimed in claim 1, wherein a distillate which comprises aldehydes and olefins and has been separated off from a hydroformylation mixture and a hydroformylation mixture are used for producing the feed mixture of aldehyde and olefin.

13. The process as claimed in claim 11, wherein the hydroformylation mixture is a decatalyzed hydroformulation mixture.

14. The process as claimed in claim 1, further comprising:
   hydrogenating a mixture obtained from the last hydroformylating stage.

15. The process as claimed in claim 1, further comprising:
   separating one or more unreacted olefins from a hydroformylation mixture obtained from the hydroformylating of one or more hydroformylating stages after removing the catalyst.

16. The process as claimed in claim 15, further comprising:
   recirculating unreacted olefins to one or more of the hydroformylating stages.

* * * * *